United States Patent
Guo et al.

(10) Patent No.: US 9,678,923 B2
(45) Date of Patent: Jun. 13, 2017

(54) PARTICLE DISPENSING APPARATUS AND METHOD

(71) Applicant: Bio-Rad Laboratories, Inc., Hercules, CA (US)

(72) Inventors: Kun Guo, Pinole, CA (US); Paul J Patt, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 1051 days.

(21) Appl. No.: 13/861,143

(22) Filed: Apr. 11, 2013

(65) Prior Publication Data

US 2013/0270287 A1    Oct. 17, 2013

Related U.S. Application Data

(60) Provisional application No. 61/623,136, filed on Apr. 12, 2012.

(51) Int. Cl.
| | |
|---|---|
| G01F 17/00 | (2006.01) |
| G01N 15/00 | (2006.01) |
| G01N 15/02 | (2006.01) |
| G06F 17/00 | (2006.01) |
| B01L 3/02 | (2006.01) |
| B01L 3/00 | (2006.01) |

(Continued)

(52) U.S. Cl.
CPC ............ *G06F 17/00* (2013.01); *B01L 3/0289* (2013.01); *G01N 15/02* (2013.01); *B01L 2200/0652* (2013.01); *B01L 2200/0657* (2013.01); *B01L 2200/143* (2013.01); *B01L 2400/0439* (2013.01); *B01L 2400/0478* (2013.01); *B01L 2400/0481* (2013.01); *G01N 15/0205* (2013.01); *G01N 2015/1062* (2013.01); *G01N 2015/1486* (2013.01)

(58) Field of Classification Search
CPC ..... B01L 2200/0652; B01L 2200/0657; B01L 2200/143; B01L 2400/0439; B01L 2400/0478; B01L 2400/0481; B01L 3/0289; G01N 2015/1062; G01N 2015/1486; G01N 17/00
See application file for complete search history.

(56) References Cited

U.S. PATENT DOCUMENTS

| | | | |
|---|---|---|---|
| 3,557,352 A | 1/1971 | Hogg et al. | |
| 5,296,910 A * | 3/1994 | Cole | G01P 5/26 356/28.5 |

(Continued)

FOREIGN PATENT DOCUMENTS

CN    101437558 A    5/2009

OTHER PUBLICATIONS

International Search Report and Written Opinion from PCT/US2013/036152, dated Aug. 8, 2013.

*Primary Examiner* — Jennifer Wecker
(74) *Attorney, Agent, or Firm* — Kilpatrick, Townsend and Stockton LLP

(57) ABSTRACT

Particles are dispensed under controlled conditions to achieve an accurate number of particles by passing a suspension of the particles through a particle detecting device, obtaining a cumulative particle count, comparing the cumulative particle count with a target value, and shutting off the suspension flow once the particle count reaches the target value, all performed by automated means.

18 Claims, 4 Drawing Sheets

(51) Int. Cl.
 *G01N 15/10* (2006.01)
 *G01N 15/14* (2006.01)

(56) References Cited

U.S. PATENT DOCUMENTS

| | | | |
|---|---|---|---|
| 5,504,272 A * | 4/1996 | Uchiyama | G03G 9/0819 399/277 |
| 5,647,386 A * | 7/1997 | Kaiser | B08B 3/12 134/111 |
| 5,978,435 A * | 11/1999 | Christensen | G01N 15/1456 377/10 |
| 6,987,228 B1 | 1/2006 | MacMichael et al. | |
| 7,345,758 B2 * | 3/2008 | van den Engh | G01N 15/1434 356/317 |
| 7,358,451 B2 | 4/2008 | MacMichael et al. | |
| 7,397,232 B2 | 7/2008 | Hu et al. | |
| 7,413,666 B2 * | 8/2008 | Bryant | C02F 1/008 210/745 |
| 7,868,260 B2 | 1/2011 | MacMichael et al. | |
| 2001/0036424 A1 * | 11/2001 | Takahashi | B01J 19/0046 422/504 |
| 2001/0041449 A1 * | 11/2001 | Ito | H01J 37/32862 438/706 |
| 2003/0041969 A1 * | 3/2003 | Schneider | B08B 3/08 156/345.15 |
| 2003/0167822 A1 * | 9/2003 | Johnson | B01L 3/021 73/1.16 |
| 2003/0170613 A1 | 9/2003 | Straus | |
| 2004/0142463 A1 | 7/2004 | Walker et al. | |
| 2005/0173313 A1 | 8/2005 | Tyvoll et al. | |
| 2007/0255199 A1 * | 11/2007 | Dewey | A61M 5/14216 604/67 |
| 2008/0255705 A1 * | 10/2008 | Degeal | B07C 5/342 700/273 |
| 2009/0050542 A1 | 2/2009 | Leary et al. | |
| 2010/0003715 A1 * | 1/2010 | Pellegrino | G01N 21/6486 435/35 |
| 2011/0243793 A1 * | 10/2011 | Kalin | H02P 21/06 422/67 |

* cited by examiner

PARTICLE DISPENSING APPARATUS AND METHOD

CROSS-REFERENCE TO RELATED PATENT APPLICATIONS

The present application claims benefit of priority to U.S. Provisional Patent Application No. 61/623,136, filed on Apr. 12, 2012, which is incorporated by reference.

BACKGROUND OF THE INVENTION

The need to dispense particles in known amounts arises in a variety of procedures. Biological cells are examples of particles that often require dispensing in known amounts. Accurate and consistent dispensing of biological cells is important in the field of biomicrofluidics notably in mass and energy transport studies, and particularly in automated microfluidic devices, as well as in morphological studies and the long-term monitoring of cells. Dispensing equipment currently available is typically designed to dispense a given volume of liquid such as a cell suspension, but the number of cells in the dispensed volume is subject to variation due to such factors as adherence of the cells to each other, and disintegration, clumping, coagulation, and even mutation of the cells. Moreover, liquid-measuring dispensing methods are particularly unreliable in terms of cell count when the number of cells to be dispensed is small, such as less than 100. The most widely used dispensing devices are air displacement pipettes, which are micropipettes operated by air-driven pistons. These deliver accurate quantities of a liquid suspension in small volumes, but the number of cells in the delivered volume is still variable and uncertain. Other devices are those employing robotics for selecting and transporting individual cells. An example is the "CellBot" system of CSEM Microfluidics (Newchatel, Switzerland). Systems of this type require individual identification and transport of each cell. Still other devices dispense known amounts of droplets. An example is the JP D300 Digital Dispenser of Tecan Systems, Inc. (San Jose, Calif., USA). This type of system does not control actual cell counts, however.

SUMMARY OF THE INVENTION

The present invention resides in a method and apparatus for accurately and efficiently dispensing a selected number of particle(s) (i.e., one or more) in a particle suspension by passing the particles through a particle counter into a collection vessel and using automation to suspend the passage of the particles into the vessel once the counter detects the passage of the selected number, also referred to herein as the "target number," of particles. The particle counter is a particle detecting device that detects the particles as they pass through a detecting area, and an automated controller cumulatively records the number of particles detected, compares this number with the target number, and halts the flow into the collection vessel once the target number is reached, resulting in the vessel containing the target number of particles. The method may also include selecting the target number and programming that number into the controller. Apparatus for performing this procedure includes the particle detecting device, a pump or other conveyance device or means for conveying the particle suspension from a source vessel through the detecting area of the particle detection device and into the collection vessel, a device for shutting off flow to or from the pump or into the collection vessel that is operable by a remotely generated signal, and a controller to record the number of particles detected, compare the number with the target, and send a signal to the shut-off device. The invention does not require, and preferably does not include, measurement or detection of the volume of suspension that is dispensed along with the particles. Certain examples of apparatus and methods within the scope of this invention include additional features such as diluent receptacles and conduits to perform dilution of the suspension at any of various points along the flow path of the suspension from its source to the collection vessel, and in some cases two or more particle counters to provide multiple counts for verification or confirmatory purposes.

In some embodiments, an apparatus for dispensing a target number of particles from a source of a suspension of said particles into a collection vessel is provided. In some embodiments, the apparatus comprises:

a particle detecting device that has a detecting area and that detects particles passing through said detecting area;

a conveyance device for conveying said suspension from said source through said detecting area and into said collection vessel; and a controller for automated counting of particles passing through said detecting area and thereby obtaining a cumulative number of particles so detected, for comparing said cumulative number with said target number, and for generating a signal when said cumulative number equals said target number; and a shutoff device for interrupting flow of said suspension into said collection vessel upon receipt of said signal.

In some embodiments, said conveyance device is a syringe pump with a piston, and said shutoff device comprises a component for suspending motion of said piston. In some embodiments, said conveyance device is a piezoelectric diaphragm pump driven by a power supply, and said shutoff device comprises a component for deactivating said power supply. In some embodiment, said conveyance device is a pressure pump, and said shutoff device comprises a solenoid valve on either an intake side or a discharge side of said pump. In some embodiments, said conveyance device is a peristaltic pump driven by a motor, and said shutoff device comprises a component for deactivating said motor. In some embodiments, said conveyance device is an electrophoretic pump driven by an electric field, and said shutoff device comprises a component for removing said electric field. In some embodiments, said conveyance device is a surface acoustic wave pump driven by a power source, and said shutoff device comprises a component for deactivating said power source. In some embodiments, said conveyance device is a pump arranged to draw said suspension from said source and to discharge said suspension into said particle detecting device. In some embodiments, said conveyance device is a pump arranged to draw said suspension from said source through said particle detecting device.

In some embodiments, said particle detecting device is a Coulter principle device detecting perturbations in an electric field caused when a particle enters said field. In some embodiments, said particle detecting device is a flow cytometer. In some embodiments, said particle detecting device is an optical camera. In some embodiments, said controller is a microcontroller or a printed circuit board.

In some embodiments, the apparatus further comprises a device for diluting said suspension with a dilution liquid upstream of said collection vessel.

In some embodiments, said particle detecting device is defined as a first particle detecting device, said detecting area is defined as a first detecting area, and said signal is defined as a first signal, said apparatus further comprising: a second particle detecting device having a second particle detecting area arranged to receive said suspension emerging from said first particle detecting device; a second controller for automated counting of particles passing through said second detecting area and thereby obtaining a confirmatory cumulative number of particles so detected, for comparing said confirmatory cumulative number with said target number, and for generating a second signal when said confirmatory cumulative number equals said target number; and a second device for diluting said suspension with a diluting liquid upstream of said first particle detecting area and for further diluting said suspension with said diluting liquid between said first particle detecting area and said second particle detecting area; and wherein said shutoff device is actuated by either said first signal or said second signal.

Also provided is a method for dispensing a target number of particle(s) into a collection vessel from a suspension of said particles in a suspending liquid. In some embodiments, said method comprises:

(a) passing said suspension through a detecting area of a particle detecting device, and detecting said particle(s) as said particle(s) pass through said detecting area, (b) cumulatively recording by a controller the number of particles so detected and comparing the cumulative number so recorded with said target number, while collecting all particles so detected in said collection vessel, and (c) by said controller, interrupting flow of said suspension into said collection vessel when said cumulative number equals said target number, thereby limiting said particles in said collection vessel to said target number.

In some embodiments, step (a) comprises pumping said suspension by a syringe pump through motion of a piston in said syringe pump, and step (c) comprises interrupting said flow by suspending motion of said piston. In some embodiments, step (a) comprises pumping said suspension by a piezoelectric diaphragm pump driven by a power supply, and step (c) comprises interrupting said flow by deactivating said power supply. In some embodiments, step (a) comprises pumping said suspension by a pressure pump, and step (c) comprises interrupting said flow by closing a solenoid valve on either an intake side or a discharge side of said pump. In some embodiments, step (a) comprises pumping said suspension by a peristaltic pump driven by a motor, and step (c) comprises interrupting said flow by deactivating said motor. In some embodiments, step (a) comprises pumping said suspension by an electrophoretic pump driven by an electric field, and step (c) comprises interrupting said flow by removing said electric field. In some embodiments, step (a) comprises pumping said suspension by a surface acoustic wave pump driven by a power source, and step (c) comprises interrupting said flow by deactivating said power source. In some embodiments, step (a) comprises pumping said suspension from a source vessel by a pump arranged to draw said suspension from said source vessel and to discharge said suspension into said particle detecting device. In some embodiments, step (a) comprises pumping said suspension from a source vessel through said particle detecting device by a pump arranged to draw said suspension from said source vessel through said particle detecting device.

In some embodiments, said particle detecting device is a Coulter principle device detecting perturbations in an electric field caused when a particle enters said field. In some embodiments, said particle detecting device is a flow cytometer, and step (b) comprises detecting said particles with a photomultiplier tube. In some embodiments, said particle detecting device is a digital optical camera, and step (b) comprises detecting said particles with a CCD or a CMOS.

In some embodiments, said controller is a microcontroller or a printed circuit board.

In some embodiments, the method further comprises diluting said suspension with a dilution liquid prior to collecting said particle(s) in said collection vessel. In some embodiments, said step of diluting said suspension is performed by continuously feeding said dilution liquid into said suspension downstream of said detecting area. In some embodiments, the method further comprises diluting said suspension with a dilution liquid prior to passing said suspension through said detecting area.

In some embodiments, said detecting area is defined as a first detecting area and said particle detecting device is defined as a first particle detecting device, said method further comprising:

(a') passing said suspension emerging from said first detecting area through a second detecting area of a second particle detecting device, and detecting said particles as they pass through said second detecting area prior to collecting said particles in said collection vessel, (a") diluting said suspension with a dilution liquid prior to passing said suspension through said first detecting area, and (a''') further diluting said suspension with said dilution liquid between said first detection area and said second detection area, and wherein step (b) comprises cumulatively recording by said controller the number of particles detected by said second particle detecting device.

Still further features, advantages, objects, and embodiments of the invention will be apparent from the descriptions that follow.

DESCRIPTION OF SELECTED EMBODIMENTS

Figure 1:
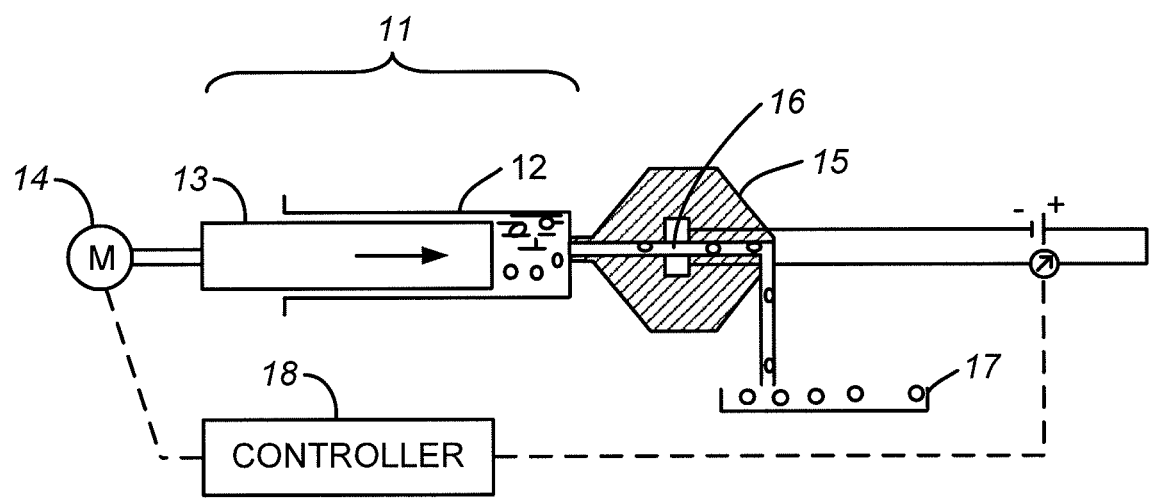
FIG. 1 is a schematic representation of one example of a particle dispensing apparatus and method in accordance with the present invention.

A variety of particle detecting and counting devices can be used in the practice of this invention. One example are devices using the Coulter principle, in which an electric field is established between electrodes on opposing sides of an orifice and the current between the electrodes measured. As a particle passes through the orifice, the current drops in view of the relatively low electrical conductivity of the particle relative to that of the suspending liquid. Descriptions of devices utilizing the Coulter principle are found in Coulter U.S. Pat. No. 2,656,508, issued Oct. 20, 1953, and Hu et al. U.S. Pat. No. 7,397,232 B2, issued Jul. 8, 2008. Other examples of particle detecting and counting devices are flow cytometers, and optical cameras. Examples of detecting components for these devices are capacitance sensors, photomultiplier tubes, CCDs (charge coupled devices), particularly linear CCDs, CMOS (complementary metal oxide semiconductors), and photodiodes. A flow cytometer with a photomultiplier tube and a digital optical camera with a CCD, particularly a linear CCD, a CMOS, or any other optical sensor, are specific examples of integrated detecting and counting devices.

In the practice of the invention, the suspension can be passed through the particle detector or counter by a variety of methods. Gravity flow can be used, although greater control over flow rate can generally be obtained by using a pump. Examples of suitable pumps are syringe pumps, piezoelectric diaphragm pumps, pressure pumps, electrophoretic pumps, and surface acoustic wave pumps. Mechanisms for suspending the flow by remote signals will vary with the type of conveying mechanism. Gravity flow can be halted by a motor valve or solenoid valve. For a syringe pump, the piston can be motor-driven and a signal can deactivate the motor and thereby suspend the movement of the piston. A piezoelectric diaphragm pump controlled by a power supply can be stopped by deactivating or disconnecting the power supply. A peristaltic pump can be stopped by deactivating the motor driving the moving part of the pump. A pressure pump can be stopped by closing a valve on either the intake side of the pump or the discharge side. Indeed, shut-off valves can be used on any pump, and examples of remotely controlled shut-off valves are solenoid valves and pneumatically operated valves. Electrophoretic pumps are effective in moving charged particles and operate by imposing an electric field on the suspension. An electrophoretic pump can be stopped by simply disconnecting the power source that supplies the electric field. A surface acoustic wave pump can be stopped by turning off the power source that creates the waves. Other examples will be readily apparent to those skilled in the art. Stoppage of flow into the collection vessel can also be achieved by diverting the flow from the collection vessel to a separate vessel or to waste. Such diversion can be achieved by a conventional rotary valve.

When a pump is used, the location of the pump relative to the other components of the system including the source vessel for the particle suspension, the particle detector, and the collection vessel, can vary. In certain embodiments, the pump is positioned between the suspension source vessel and the particle detector. In this position, the pump draws the suspension from the source vessel and forces the suspension from the discharge side of the pump through the particle detector and from there into the collection vessel. In other embodiments, both the source vessel and the particle detector are positioned on the intake side of the pump, and the pump thereby draws the suspension through the particle detector. The collection vessel can reside on either the discharge side of the pump or, if the pump draws air from above the liquid levels, on the intake side.

The signal that terminates the collection of the particles, either by deactivating the pump, closing or turning a valve, or generally stopping flow into or diverting flow from the collection vessel, can be an electrical signal, a pneumatic signal, an electromagnetic signal, an optical signal or any other conventional signal that can be generated by automated means and transmitted to the component that terminates the collection, whether that component is a motor driving the pump, a valve on either side of the pump or leading to the collection vessel, or any other such component.

Automation for counting the particle(s), comparing the particle count with the target value, and transmitting a signal to an appropriate site in the system for stopping or diverting the flow can be achieved by conventional means, examples of which are a microcontroller, a printed circuit board, and a computer console. As noted above, programmable devices, particularly to allow the user to set the target number, are particularly useful. Examples of programmable microcontrollers are those with internal EPROM or EEPROM and programmable interface controllers in general.

Dilution of the particle suspension during the counting stage, the collecting stage, or both can be useful in many cases. Dilution may facilitate the counting or dispensing of very small numbers of particles, and may also be of value in the uses of particles once they have been dispensed. Dilution can be achieved by pumping a diluent liquid into the flowing suspension. The diluent can be any liquid that is compatible and miscible with the suspending liquid of the starting suspension and that will not damage the particles. The diluent can thus be identical or similar to the suspending liquid, but can also contain additives that enhance the dispensing function such as anticoagulation agents, or additives that are useful in the procedures to which the particles will be exposed to after they are dispensed, such as nutrients for cell growth procedures, for example. The introduction of a diluent can be used in systems that include multiple particle counters, as mentioned above, to allow counting to be performed on both the undiluted and diluted suspensions or after different stages of dilution.

One or more particles that can be dispensed by the apparatus and methods of this invention include solid particles of synthetic materials such as microbeads, droplets of liquids that are suspended in a liquid in which the droplets are immiscible, and biological bodies such as vesicles, organelles, liposomes, and living cells.

FIG. 1 presents one example of a particle dispensing apparatus in accordance with present invention. A syringe pump 11 is used to move a suspension of cells through the apparatus. The barrel 12 of the syringe serves as the source vessel for the suspension, and the syringe piston 13 is driven by a motor 14 to mobilize the suspension. As it leaves the syringe barrel 12, the suspension passes through a particle detector 15 that operates by the Coulter principle, counting the cells that pass through a particle detecting area 16 within the detector. The cells are collected in a collection vessel 17 as they are counted. The collection vessel 17 can be a Petri dish, a microtube, or any receptacle in which a procedure involving a precise number of cells is to be performed. A controller 18 receives a value from the particle detector representing the cell count, compares the count to a target value, and controls the syringe motor 14 to stop the flow of suspension once the target value is reached.

Figure 2:
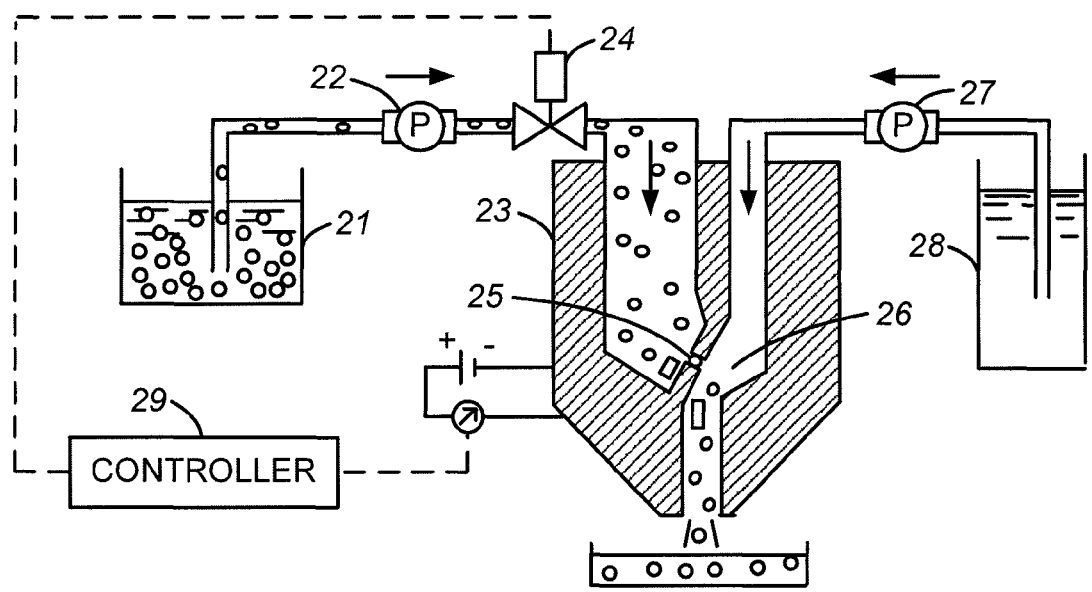
FIG. 2 is a schematic representation of a second example within the scope of the invention.

FIG. 2 presents a second example, one that includes dilution of the suspension. In this example, the suspension source is an open vessel 21 from which the suspension is drawn by a pump 22. The particle counter 23 is on the discharge side of the pump and is separated from the pump by a solenoid valve 24. Detection of cells in the particle detecting area 25 is performed on the same principle as that used in FIG. 1. Downstream of the particle detecting area 25 is a mixing area 26 where suspension emerging from the particle detecting area 25 is mixed with a dilution liquid supplied by a separate pump 27 from a diluent vessel 28. A controller 29 governs the solenoid valve 24 based on the signal from the particle counter, and the diluted cell suspension containing an accurately known number of cells is received by the collection vessel 30.

Figure 3:
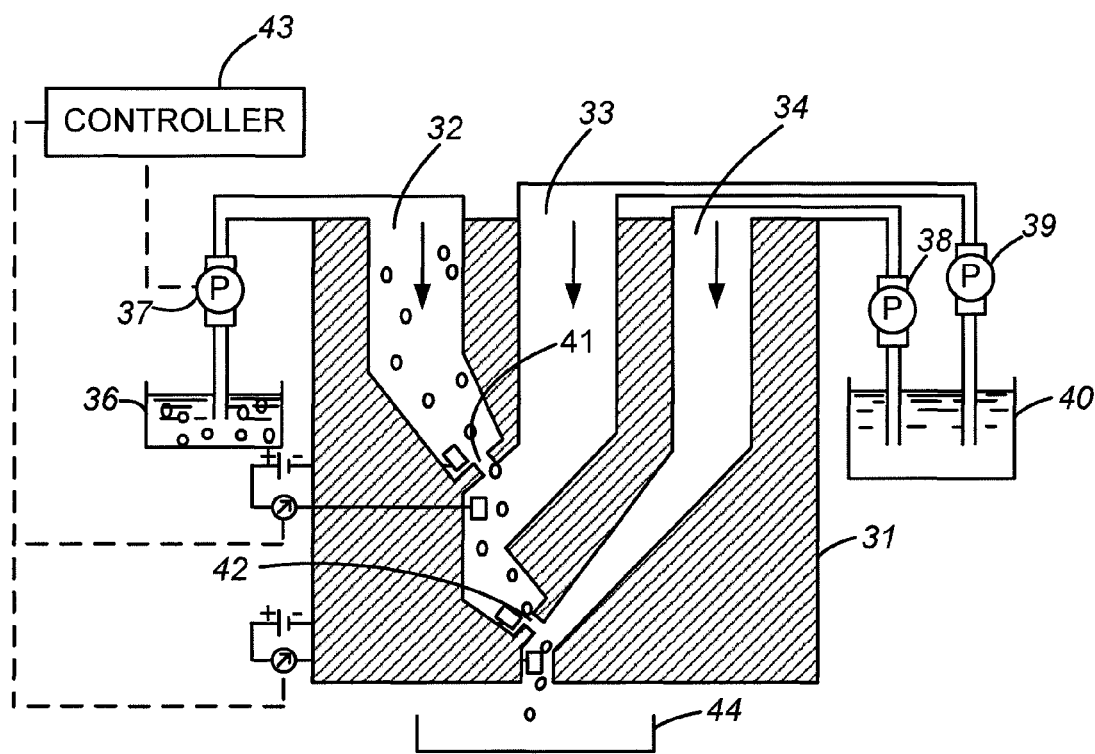
FIG. 3 is a schematic representation of a third example within the scope of the invention.

FIG. 3 illustrates an apparatus with two detection mechanisms and two dilutions of the suspension, but utilizes the same principles as the apparatus of FIG. 2. The particle detecting device 31 in this example has three internal passages—one passage for the undiluted suspension 32 and two passages 33, 34 for diluent. The particle suspension passage 32 is supplied by a suspension source vessel 36 and driven by a pump 37, while the diluent passages 33, 34 are supplied by individual pumps 38, 39 drawing from a single diluent source vessel 40. The particle detecting device 31 includes two particle detecting areas 41, 42, each equipped with a separate pair of electrodes detecting cells by use of the Coulter principle and sending separate signals to the controller 43. The first diluent passage 33 supplies diluent immediately downstream of the first particle detecting area 41, while the second diluent passage 34 supplies further diluent downstream of the second particle detecting area 42. The controller 43 compares both signals to the target count and sends a governing signal to the suspension pump 37. The twice-diluted particle suspension with an accurately known number of particles is dispensed into the collection vessel 44.

Figure 4:
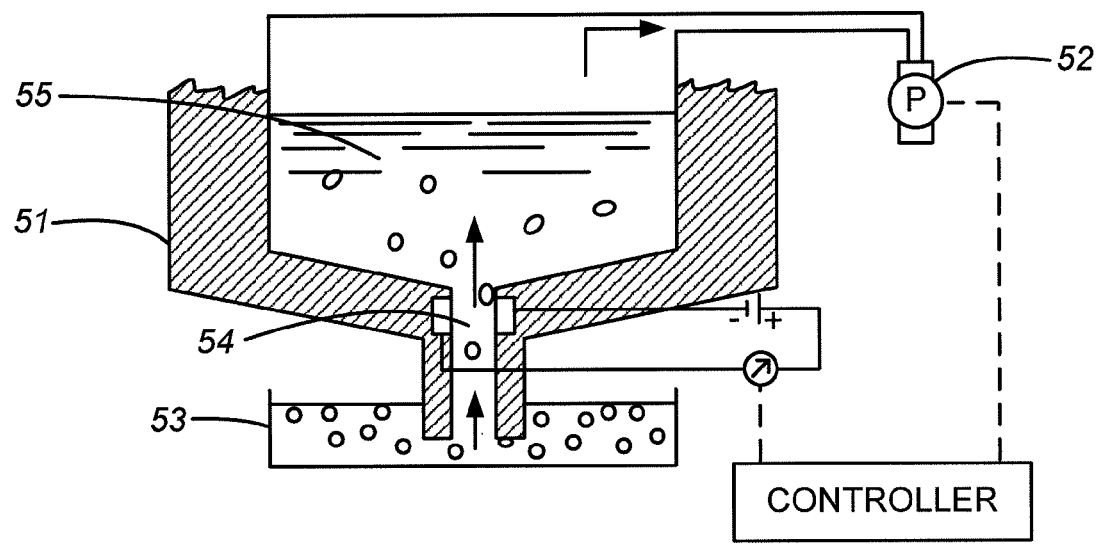
FIG. 4 is a schematic representation of a fourth example within the scope of the invention.

A fourth example is shown in FIG. 4. In this example, the particle detecting device 51 is on the intake or suction side of the pump 52, and the pump draws the particle suspension from the suspension source vessel 53 through the particle detecting area 54 by applying a vacuum to these components. An interior cavity 55 in the particle detecting device 51 serves as the collection vessel. Once the volume of suspension with counted particles has entered the interior cavity 55, it can be dispensed to another collection vessel by the same pump.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. Apparatus for dispensing a target number of particles from a source of a suspension of said particles into a collection vessel, said apparatus comprising:
   a particle detecting device that has a detecting area and that detects particles passing through said detecting area;
   a conveyance device for conveying said suspension from said source through said detecting area and into said collection vessel;
   a mixing area downstream of said detecting area;
   a pump for supplying a dilution liquid from a diluent vessel to said mixing area;
   a controller for automated counting of particles passing through said detecting area and thereby obtaining a cumulative number of particles so detected, for comparing said cumulative number with said target number, and for generating a signal when said cumulative number equals said target number; and
   a shutoff device for interrupting flow of said suspension into said collection vessel upon receipt of said signal.

2. The apparatus of claim 1 wherein said conveyance device is a syringe pump with a piston, and said shutoff device comprises a component for suspending motion of said piston.

3. The apparatus of claim 1 said conveyance device is a piezoelectric diaphragm pump driven by a power supply, and said shutoff device comprises a component for deactivating said power supply.

4. The apparatus of claim 1, wherein said conveyance device is a pressure pump, and said shutoff device comprises a solenoid valve on either an intake side or a discharge side of said pump; or
   wherein said conveyance device is a peristaltic pump driven by a motor, and said shutoff device comprises a component for deactivating said motor; or
   wherein said conveyance device is an electrophoretic pump driven by an electric field, and said shutoff device comprises a component for removing said electric field; or
   wherein said conveyance device is a surface acoustic wave pump driven by a power source, and said shutoff device comprises a component for deactivating said power source; or
   wherein said conveyance device is a pump arranged to draw said suspension from said source and to discharge said suspension into said particle detecting device; or
   wherein said conveyance device is a pump arranged to draw said suspension from said source through said particle detecting device.

5. The apparatus of claim 1 wherein said particle detecting device is a Coulter principle device detecting perturbations in an electric field caused when a particle enters said field.

6. The apparatus of claim 1 wherein said particle detecting device is a flow cytometer.

7. The apparatus of claim 1 wherein said particle detecting device is an optical camera.

8. The apparatus of claim 1 wherein said controller is a microcontroller or a printed circuit board.

9. The apparatus of claim 1 wherein said particle detecting device is defined as a first particle detecting device, said detecting area is defined as a first detecting area, and said signal is defined as a first signal, said apparatus further comprising:
   a second particle detecting device having a second particle detecting area arranged to receive said suspension emerging from said first particle detecting device;
   a second controller for automated counting of particles passing through said second detecting area and thereby obtaining a confirmatory cumulative number of particles so detected, for comparing said confirmatory cumulative number with said target number, and for generating a second signal when said confirmatory cumulative number equals said target number; and
   a second device for diluting said suspension with a diluting liquid upstream of said first particle detecting area and for further diluting said suspension with said diluting liquid between said first particle detecting area and said second particle detecting area;
   and wherein said shutoff device is actuated by either said first signal or said second signal.

10. A method for dispensing a target number of particle(s) into a collection vessel from a suspension of said particles in a suspending liquid, said method comprising:
   (a) passing said suspension through a detecting area of a particle detecting device, and detecting said particle(s) as said particle(s) pass through said detecting area,
   (b) cumulatively recording by a controller the number of particles so detected and comparing the cumulative number so recorded with said target number,
   (c) mixing said suspension with a dilution liquid downstream of said detecting area, (d) collecting all particles so detected in said collection vessel, and (e) by said controller, interrupting flow of said suspension into said collection vessel when said cumulative number equals said target number, thereby limiting said particles in said collection vessel to said target number.

11. The method of claim 10 wherein step (a) comprises pumping said suspension by a syringe pump through motion of a piston in said syringe pump, and step (e) comprises interrupting said flow by suspending motion of said piston; or wherein step (a) comprises pumping said suspension by a piezoelectric diaphragm pump driven by a power supply, and step (e) comprises interrupting said flow by deactivating said power supply; or wherein step (a) comprises pumping said suspension by a pressure pump, and step (e) comprises interrupting said flow by closing a solenoid valve on either an intake side or a discharge side of said pump; or wherein step (a) comprises pumping said suspension by a peristaltic pump driven by a motor, and step (e) comprises interrupting said flow by deactivating said motor; or wherein step (a) comprises pumping said suspension by an electrophoretic pump driven by an electric field, and step (e) comprises interrupting said flow by removing said electric field; or wherein step (a) comprises pumping said suspension by a surface acoustic wave pump driven by a power source, and step (e) comprises interrupting said flow by deactivating said power source; or wherein step (a) comprises pumping said suspension from a source vessel by a pump arranged to draw said suspension from said source vessel and to discharge said suspension into said particle detecting device; or wherein step (a) comprises pumping said suspension from a source vessel through said particle detecting device by a pump arranged to draw said suspension from said source vessel through said particle detecting device.

12. The method of claim 10 wherein said particle detecting device is a Coulter principle device detecting perturbations in an electric field caused when a particle enters said field.

13. The method of claim 10 wherein said particle detecting device is a flow cytometer, and step (a) comprises detecting said particles with a photomultiplier tube.

14. The method of claim 10 wherein said particle detecting device is a digital optical camera, and step (a) comprises detecting said particles with a CCD or a CMOS.

15. The method of claim 10 wherein said controller is a microcontroller or a printed circuit board.

16. The method of claim 10 wherein said step of mixing said suspension is performed by continuously feeding said dilution liquid into said suspension downstream of said detecting area.

17. The method of claim 10 further comprising diluting said suspension with a dilution liquid prior to passing said suspension through said detecting area.

18. The method of claim 10 wherein said detecting area is defined as a first detecting area and said particle detecting device is defined as a first particle detecting device, said method further comprising:

(a') passing said suspension emerging from said first detecting area through a second detecting area of a second particle detecting device, and detecting said particles as they pass through said second detecting area prior to collecting said particles in said collection vessel, (a") diluting said suspension with a dilution liquid prior to passing said suspension through said first detecting area, and (a''') further diluting said suspension with said dilution liquid between said first detection area and said second detection area, and wherein step (b) comprises cumulatively recording by said controller the number of particles detected by said second particle detecting device.

\* \* \* \* \*